(12) United States Patent
Okatake et al.

(10) Patent No.: US 6,541,637 B1
(45) Date of Patent: Apr. 1, 2003

(54) METHOD FOR DRYING ANHYDROUS PAROXETINE HYDROCHLORIDE

(75) Inventors: Mitsuru Okatake, Osaka (JP); Taro Ishibashi, Osaka (JP); Yoshihiro Kawata, Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/445,598

(22) PCT Filed: Apr. 12, 1999

(86) PCT No.: PCT/JP99/01914
§ 371 (c)(1),
(2), (4) Date: Dec. 13, 1999

(87) PCT Pub. No.: WO99/52902

PCT Pub. Date: Oct. 21, 1999

(30) Foreign Application Priority Data

Apr. 13, 1998 (JP) ............................................. 10-101058

(51) Int. Cl.[7] ..................... C07D 405/12; A61K 31/445
(52) U.S. Cl. ........................................ 546/197; 514/321
(58) Field of Search ............................ 514/321; 546/197

(56) References Cited

U.S. PATENT DOCUMENTS 5,872,132 A * 2/1999 Ward et al. .................. 514/321
5,948,914 A * 9/1999 Sugi et al. ................... 546/240

FOREIGN PATENT DOCUMENTS

| EP | 0812827 A | 12/1997 |
| JP | 08245620 A | 9/1996 |
| JP | 10-291975 | 11/1998 |
| WO | 96 24595 | 8/1998 |
| WO | WO 0008017 A1 | 2/2000 |

OTHER PUBLICATIONS

Aldrich catalog, p. 1431, 1998.*

* cited by examiner

*Primary Examiner*—Ceila Chang
(74) *Attorney, Agent, or Firm*—Birch, Stewart, Kolasch & Birch, LLP

(57) ABSTRACT

A process for drying paroxetine hydrochloride anhydrate comprising (A) reacting a paroxetine compound with hydrogen chloride in the presence of isopropyl alcohol and crystallizing the resulting product, to obtain paroxetine hydrochloride anhydrate, and drying the resulting paroxetine hydrochloride anhydrate at a temperature of not more than 60° C. and under normal pressure or lower in an atmosphere which does not substantially contain moisture until the content of isopropyl alcohol attains to not more than 15% by weight; and (B) further drying the paroxetine hydrochloride anhydrate at a temperature of 80° to 110°C. in an atmosphere reduced to not more than 20 mm Hg until the content of isopropyl alcohol attains to not more than 5% by weight. According to the present invention, the amount of remaining isopropyl alcohol contained in the paroxetine hydrochloride anhydrate, crystallized in the presence of isopropyl alcohol, can be efficiently reduced in a short period of time without necessitating a large-scaled apparatus.

5 Claims, No Drawings

METHOD FOR DRYING ANHYDROUS PAROXETINE HYDROCHLORIDE

This application is the national phase under 35 U.S.C. §371 of PCT International Application No. PCT/JP99/01914 which has an International filing date of Apr. 12, 1999, which designated the United States of America.

TECHNICAL FIELD

The present invention relates to a process for drying paroxetine hydrochloride anhydrate. More specifically, the present invention relates to a process for drying paroxetine hydrochloride anhydrate to reduce the amount of remaining isopropyl alcohol.

BACKGROUND ART

Paroxetine hydrochlorides such as paroxetine hydrochloride anhydrate are useful compounds as antidepressants.

Conventionally, paroxetine hydrochloride anhydrate obtained by reacting paroxetine with hydrogen chloride in the presence of isopropyl alcohol contains isopropyl alcohol. Therefore, in order not to deform its crystal form, the paroxetine hydrochloride anhydrate is dried by a vacuum drying process employing a vacuum oven which is temperature-adjusted to a temperature lower than 80° C. However, it has been difficult to sufficiently remove isopropyl alcohol contained in the paroxetine hydrochloride anhydrate by the vacuum drying process. Therefore, there is a defect in the process such that a long period of time of not less than about 100 hours is required to dry until the content of isopropyl alcohol attains to not more than 5% by weight.

Therefore, as a process capable of eliminating the above defect, there has been proposed a process comprising isolating the paroxetine hydrochloride anhydrate containing isopropyl alcohol, drying under vacuum, removing isopropyl alcohol liberated from or not bonded to the paroxetine hydrochloride anhydrate, and thereafter replacing isopropyl alcohol bonded to the paroxetine hydrochloride anhydrate with a substituting agent such as water or supercritical carbon dioxide [Japanese Patent Laid-Open No. Hei 8-245620, column 9, lines 1 to 9].

However, in this process, when water (steam) is used as a substituting agent, there is a possibility of causing crystal conversion to paroxetine hydrochloride hemihydrate, and there is a defect that complicated procedures such that the replaced moisture should be removed by vacuum drying are necessitated. In addition, when the supercritical carbon dioxide is used, since carbon dioxide must be pressurized to a high pressure of 2500 psi (170 atm.) or so during the course of preparing the supercritical carbon dioxide [Ibid, column 20, lines 19 to 38], there arises a defect that a large-scaled apparatus for preparing supercritical carbon dioxide is required.

Accordingly, since complicated procedures and large-scaled apparatus are necessary for the conventional processes for drying paroxetine hydrochloride anhydrate, there is a defect such that the processes are poor in production efficiency.

An object of the present invention is to provide a process for drying paroxetine hydrochloride anhydrate capable of efficiently reducing the amount of remaining isopropyl alcohol in the paroxetine hydrochloride anhydrate, which is obtained by crystallizing in the presence of isopropyl alcohol, without the necessity of a large-scaled apparatus.

DISCLOSURE OF INVENTION

According to the present invention, there can be provided a process for drying paroxetine hydrochloride anhydrate comprising:

(A) reacting a paroxetine compound with hydrogen chloride in the presence of isopropyl alcohol and crystallizing the resulting product, to obtain paroxetine hydrochloride anhydrate, and drying the resulting paroxetine hydrochloride anhydrate at a temperature of not more than 60° C. and under normal pressure or lower in an atmosphere which does not substantially contain moisture until the content of isopropyl alcohol attains to not more than 15% by weight; and (B) further drying the paroxetine hydrochloride anhydrate at a temperature of 80° to 110° C. in an atmosphere reduced to not more than 20 mm Hg until the content of isopropyl alcohol attains to not more than 5% by weight.

BEST MODE FOR CARRYING OUT THE INVENTION

As described above, the drying process of the present invention employs a two-step drying process comprising:

(A) reacting a paroxetine compound with hydrogen chloride in the presence of isopropyl alcohol and crystallizing the resulting product, to obtain paroxetine hydrochloride anhydrate, and drying the resulting paroxetine hydrochloride anhydrate at a temperature of not more than 60° C. and under normal pressure or lower in an atmosphere which does not substantially contain moisture until the content of isopropyl alcohol attains to not more than 15% by weight; and (B) further drying the paroxetine hydrochloride anhydrate at a temperature of 80° to 110° C. in an atmosphere reduced to not more than 20 mm Hg until the content of isopropyl alcohol attains to not more than 5% by weight.

The paroxetine hydrochloride anhydrate can be obtained by, for instance, a process comprising dissolving a paroxetine compound in isopropyl alcohol, and thereafter reacting the paroxetine compound with hydrogen chloride, whereby reacting the paroxetine compound with hydrogen chloride in the presence of isopropyl alcohol; and crystallizing the resulting product. This paroxetine hydrochloride anhydrate usually contains 30 to 70% by weight or so of isopropyl alcohol.

The paroxetine compound includes, for instance, paroxetine, N-tert-butoxycarbonylparoxetine, and the like. The N-tert-butoxycarbonylparoxetine is (3S,4R)-trans-1-tert-butoxycarbonyl-4-(4-fluorophenyl)-3-[3,4-methylenedioxyphenyl)oxymethyl]piperidine.

It is preferable that the amount of hydrogen chloride used in the reaction with the paroxetine compound is usually 1 to 5 mol or so per 1 mol of the paroxetine compound.

The amount of the paroxetine compound is not limited to specified ones. It is preferable that the amount of the paroxetine hydrochloride anhydrate is 5 to 60 parts by weight, based on 100 parts by weight of isopropyl alcohol.

The reaction temperature of the paroxetine compound with hydrogen chloride may be usually within the range of ambient temperature to the boiling point of isopropyl alcohol.

In addition, isopropyl alcohol may be used alone, or used in combination with, for instance, other organic solvents, organic acids, and the like in an amount which would not hinder the object of the present invention. In addition, it is preferable that water is not contained in isopropyl alcohol from the viewpoint of shortening the drying time. Therefore, it is preferable that isopropyl alcohol is substantially non-water-containing isopropyl alcohol, i.e. one having a water content of not more than 0.1%.

The reaction time is not limited to specified ones. The reaction time can be usually up to the termination of the reaction.

In the reaction solution of the formed paroxetine hydrochloride anhydrate, impurities are contained in some cases. In this case, in order to remove the impurities, the reaction solution can be treated with activated charcoal.

By gradually cooling the reaction solution, a relatively large paroxetine hydrochloride anhydrate having good filterability can be obtained as crystals.

In the crystals of the resulting paroxetine hydrochloride anhydrate, isopropyl alcohol is contained. The crystals of paroxetine hydrochloride anhydrate containing isopropyl alcohol are extremely thermally unstable. For instance, when the crystals of paroxetine hydrochloride anhydrate containing isopropyl alcohol are dried at a temperature of not less than 80° C., a portion of the crystals of paroxetine hydrochloride anhydrate is dissolved in the isopropyl alcohol contained, and thereby its crystal form is deformed, so that a desired crystal form cannot be obtained [see Comparative Example 2 described below].

In the present invention, first, this paroxetine hydrochloride anhydrate containing isopropyl alcohol is dried at a temperature of not more than 60° C. and under normal pressure or lower in an atmosphere which does not substantially contain moisture until the content of isopropyl alcohol attains to not more than 15% by weight.

One of great features of the present invention resides in that the above procedure is employed. When drying the paroxetine hydrochloride anhydrate, the paroxetine hydrochloride anhydrate would not be converted to paroxetine hydrochloride hemihydrate like prior art since the procedure is employed. In addition, there is an advantage that complicated procedures which necessitate that replaced water must be removed by vacuum drying after replacement with water (steam) are not necessitated. Further, there are not necessitated large-scale equipments for generating supercritical carbon dioxide, such as pressure apparatus and pressure vessel, when replaced with supercritical carbon dioxide, and moreover its crystal form is not deformed even when the paroxetine hydrochloride anhydrate is subsequently heated to a temperature of not less than 80° C. after the above procedures.

The atmosphere which does not substantially contain moisture refers to an atmosphere of which relative humidity (at 20° C.) is not more than 10%, preferably not more than 5%. The atmosphere which does not substantially contain moisture includes, for instance, dried air, and inert gases such as nitrogen gas and argon gas. Among these, the inert gases such as nitrogen gas and argon gas are preferable because they can easily form an atmosphere which does not substantially contain moisture.

In the course of drying the paroxetine hydrochloride anhydrate in the atmosphere which does not substantially contain moisture, the pressure of the atmosphere may be normal pressure or lower. As a drying process, there can be employed a process for drying in an open system such as through-flow drying and a process for drying in a closed system such as drying under reduced pressure. When the drying is carried out in a closed system, it is preferable that the pressure inside the system is adjusted to a reduced pressure of not more than 200 mm Hg, preferably not more than 100 mm Hg, more preferably not more than 50 mm Hg, from the viewpoint of improving drying efficiency.

The temperature in the course of drying the paroxetine hydrochloride anhydrate is not more than 60° C., preferably not more than 50° C., from the viewpoint of maintaining the crystal form of the paroxetine hydrochloride anhydrate. It is desired that the temperature is not less than 15° C., preferably not less than 20° C., from the viewpoint of improving drying efficiency.

The drying of the paroxetine hydrochloride anhydrate is carried out until the content of the isopropyl alcohol in the paroxetine hydrochloride anhydrate attains to not more than 15% by weight, preferably not more than 13% by weight. The lower limit of the content of isopropyl alcohol after drying is not limited to specified ones. However, since the drying of the paroxetine hydrochloride anhydrate can be rapidly carried out in the subsequent heating and drying procedures, it is preferable that the subsequent heating and drying procedures are carried out at a stage where the content of isopropyl alcohol attains to 8 to 15% by weight or so, from the viewpoint of shortening the time period necessary for drying.

As explained above, when the paroxetine hydrochloride anhydrate is dried at a temperature of not more than 60° C. and under normal pressure in an atmosphere which does not substantially contain water until the content of isopropyl alcohol attains to not more than 15% by weight, there is unexpectedly caused no deformation of the crystals of the paroxetine hydrochloride anhydrate even when the paroxetine hydrochloride anhydrate is further dried at a high temperature of 80° to 110° C. When the drying is terminated before the content of isopropyl alcohol in the paroxetine hydrochloride anhydrate attains to not more than 15% by weight, the crystals of the paroxetine hydrochloride anhydrate are deformed when subsequently dried at a high temperature of not less than 80° C.

The content of isopropyl alcohol in the paroxetine hydrochloride anhydrate in the course of carrying out the drying procedures can be confirmed by, for instance, gas chromatography, nuclear magnetic resonance spectroscopy (NMR), or the like.

After drying is carried out until the content of isopropyl alcohol in the paroxetine hydrochloride anhydrate attains to not more than 15% by weight, the paroxetine hydrochloride anhydrate is further dried at a temperature of 80° to 110° C. until the content of isopropyl alcohol attains to 5% by weight in an atmosphere reduced to not more than 20 mm Hg.

As described above, one of the features of the present invention also resides in that a drying procedure is carried out as a secondary step subsequently to the above drying procedure as a first step.

As described above, the paroxetine hydrochloride anhydrate is deformed in the crystal form at a temperature of not less than 80° C.

To the contrary, in the present invention, desired crystals of the paroxetine hydrochloride anhydrate can be obtained without the deformation of its crystal form, nevertheless drying is carried out at a temperature of more than 80° C., which cannot be expected from the conventional techniques.

It is thought that the reason why the above excellent effects can be exhibited would be probably based on the following reasons.

Generally, isopropyl alcohol is present on the surface of the crystals of the paroxetine hydrochloride anhydrate in an amount of about 20 to about 60% by weight based on the weight of the paroxetine hydrochloride anhydrate, and isopropyl alcohol is incorporated into the inside of the crystals in an amount of about 10 to about 15% by weight based on the weight of the paroxetine hydrochloride anhydrate. In such a state, when the temperature of crystals of the paroxetine hydrochloride anhydrate is adjusted to not less than 80° C., since the crystals of the paroxetine hydrochloride anhydrate partially or entirely dissolve in isopropyl alcohol existing on the surface of crystals, their crystal forms are considered to be deformed.

On the other hand, in the present invention, isopropyl alcohol existing on its surface is removed because the drying procedure is employed in the first step. As described above, since isopropyl alcohol existing on the surface is previously removed, even when the paroxetine hydrochloride anhydrate is heated to a temperature of not less than 80° C. at which its crystal form is thought to be deformed, it is thought that the drying of the crystals can be efficiently carried out without causing the deformation of the crystals by the dissolution of the crystals in isopropyl alcohol.

The object of the present invention cannot be achieved by simply heating the crystals to a temperature of not less than of 80° C. to remove isopropyl alcohol incorporated in the crystals. On the other hand, it is thought that drying can be efficiently carried out because the drying procedure in the second step is carried out in an atmosphere reduced to not more than 20 mm Hg, isopropyl alcohol is sequentially efficiently discharged from the inside of the crystal to its outside.

After the termination of the drying procedure in the first step and before the drying procedure in the second step, the temperature of the atmosphere is adjusted to a temperature of 80° to 110° C., and thereafter the atmosphere may be reduced to not more than 20 mm Hg. Alternatively, the atmosphere is reduced to not more than 20 mm Hg, and thereafter the temperature of the atmosphere may be adjusted to a temperature of 80° to 110° C. In addition, when the temperature is raised to 80° to 110° C. after the termination of the drying procedure in the first step, the temperature may be raised in multi-steps or continuously.

The temperature in the course of drying the paroxetine hydrochloride anhydrate is not less than 80° C., preferably not less than 90° C., from the viewpoint of the improvement of the drying efficiency, and the temperature is not more than 110° C., preferably not more than 100° C., in consideration that the melting point of the paroxetine hydrochloride anhydrate is 115° to 120° C.

It is preferable that the pressure of the atmosphere in the course of drying the paroxetine hydrochloride anhydrate is as low as possible, from the viewpoint of the shortening the drying time and maintaining the crystal form. From the above aspects, the pressure of the atmosphere is not more than 20 mm Hg, preferably not more than 10 mm Hg.

In the present invention, it is preferable that the drying procedure in the first step and the drying procedure in the second step are continuously carried out in the same system in order to efficiently carry out the drying.

When the drying is carried out in the manner described above, rapid drying can be done until the content of isopropyl alcohol contained in the paroxetine hydrochloride anhydrate attains to not more than 5% by weight, without deforming the crystal form of the paroxetine hydrochloride anhydrate. The reason why the paroxetine hydrochloride anhydrate is dried until the content of isopropyl alcohol contained in the paroxetine hydrochloride anhydrate attains to not more than 5% by weight is that the paroxetine hydrochloride anhydrate is suitably usable as pharmaceuticals; therefore, the content of a solvent is desirably as low as possible for such uses. Also, when the content of isopropyl alcohol is exceedingly reduced, a long period of time is required for drying. Therefore, it is desirable that the content of isopropyl alcohol in the paroxetine hydrochloride anhydrate is not less than 2.0% by weight, preferably not less than 2.3% by weight, more preferably 2.5% by weight.

Next, the present invention will be described in further detail on the basis of Examples, without intending to limit the present invention to these Examples.

PREPARATION EXAMPLE 1

In 137 ml of isopropyl alcohol was dissolved 16.5 g of [(−)-(3S,4R)-1-tert-butyloxycarbonyl-4-(4-fluorophenyl)-3-(3,4-methylenedioxyphenyl)oxymethylpiperidine] obtained by a process described in EP-A-812827 (1997), to give a solution. To the resulting solution, 17.5 ml of an isopropyl alcohol solution in which hydrogen chloride was dissolved (concentration of hydrogen chloride: 20% by weight) was added dropwise at about 70° C., and 0.8 g of activated charcoal was further added thereto, and the mixture was stirred for about 15 minutes.

Next, the activated charcoal was removed from the solution at a temperature of about 70° C. by filtration, and thereafter the resulting filtrate was gradually cooled to 0° to 5° C. The mixture was additionally stirred at a temperature of 0° to 5° C. for 1 hour, and the paroxetine hydrochloride anhydrate was allowed to precipitate, and the precipitate was collected by filtration under nitrogen gas stream.

The resulting crystals of the paroxetine hydrochloride anhydrate contained 53.5% by weight of isopropyl alcohol.

EXAMPLE 1

The paroxetine hydrochloride anhydrate containing 53.5% by weight of isopropyl alcohol, obtained in Preparation Example 1 was dried at room temperature (about 20° C.) under reduced pressure of 2 to 20 mm Hg for 12 hours to adjust the content of isopropyl alcohol to 9.8% by weight.

Next, drying was carried out for 10 hours under reduced pressure of 2 to 20 mm Hg, with adjusting the temperature of the crystals to 85° to 90° C. The content of isopropyl alcohol in the crystals after drying was 2.4% by weight. Its crystal form was examined by powdered X-ray diffraction and infrared absorption spectroscopy. However, no deformation was found.

From the above results, it can be seen that according to the process of Example 1, the amount of remaining isopropyl alcohol in the crystals of the paroxetine hydrochloride anhydrate containing isopropyl alcohol can be efficiently reduced to less than 2.5% by weight in a relatively short period of time of about 22 hours without using a large-scaled apparatus.

EXAMPLE 2

The crystals of the paroxetine hydrochloride anhydrate containing 53.5% by weight of isopropyl alcohol, obtained in Preparation Example 1 were dried at room temperature (about 20° C.) in nitrogen gas stream [relative humidity (20° C.): 0.1 %] for 24 hours. As a result, the content of isopropyl alcohol in the crystals of the paroxetine hydrochloride anhydrate was 12.6% by weight.

The crystals of the paroxetine hydrochloride anhydrate were dried at 80° C. for 18 hours under reduced pressure of 1 to 3 mm Hg, to give crystals of the paroxetine hydrochloride anhydrate containing 2.9% by weight of isopropyl alcohol. The crystal form of the resulting paroxetine hydrochloride anhydrate was examined by powdered X-ray diffraction and infrared absorption spectroscopy. However, no deformation was found.

From the above results, it can be seen that according to the process of Example 2, the amount of remaining isopropyl alcohol in the crystals of the paroxetine hydrochloride anhydrate containing isopropyl alcohol can be efficiently reduced to less than 3.0% by weight in a relatively short period of time of about 42 hours without using a large-scaled apparatus.

EXAMPLE 3

The paroxetine hydrochloride anhydrate was prepared in the same manner as in Preparation Example 1, to give 1423.5 g of crystals of paroxetine hydrochloride anhydrate. The crystals contained 59.3% by weight of isopropyl alcohol.

The crystals of the paroxetine hydrochloride anhydrate containing isopropyl alcohol were dried at a temperature of 50° to 60° C. and under reduced pressure of 3 to 150 mm Hg. As a result, the content of isopropyl alcohol in the crystals of the paroxetine hydrochloride anhydrate was 10.8% by weight.

Drying was carried out for 10 hours under reduced pressure of 1 to 3 mm Hg, with adjusting the temperature of the crystals to 85° to 110° C., to give crystals of paroxetine hydrochloride anhydrate containing 0.9% by weight of isopropyl alcohol. The crystal form of the paroxetine hydrochloride anhydrate was examined by powdered X-ray diffraction and infrared absorption spectroscopy. However, no deformation was found.

From the above results, it can be seen that according to the process of Example 3, the amount of remaining isopropyl alcohol in the crystals of the paroxetine hydrochloride anhydrate containing isopropyl alcohol can be efficiently reduced to less than 1.0% by weight in a relatively short period of time of about 28 hours without using a large-scaled apparatus.

EXAMPLE 4

The paroxetine hydrochloride anhydrate was prepared in the same manner as in Preparation Example 1, and thereafter an isopropyl alcohol solution containing the crystals of the paroxetine hydrochloride anhydrate was subjected to pressure filtration by nitrogen gas with a pressure filter (Druck filter). The resulting 26.0 kg of the crystals of paroxetine hydrochloride anhydrate contained 58.5% by weight of isopropyl alcohol.

The crystals of paroxetine hydrochloride anhydrate containing 58.5% by weight of isopropyl alcohol were dried in the pressure filter at the temperature of 50° C. and under reduced pressure of 10 to 80 mm Hg, and the content of isopropyl alcohol was adjusted to 13.1% by weight.

Subsequently, drying was further carried out for about 12 hours under reduced pressure of 1 to 3 mm Hg, with adjusting the temperature of the crystals of paroxetine hydrochloride anhydrate to 85° C. to dry the crystals of paroxetine hydrochloride anhydrate. The content of isopropyl alcohol in the dried crystals was 2.3% by weight. The crystal form of the paroxetine hydrochloride anhydrate was examined by powdered X-ray diffraction and infrared absorption spectroscopy. However, no deformation was found.

From the above results, it can be seen that according to the process of Example 4, the amount of remaining isopropyl alcohol in the crystals of the paroxetine hydrochloride anhydrate, obtained by crystallizing in the presence of isopropyl alcohol without using a large-scaled apparatus can be efficiently reduced to less than 2.5% by weight in a relatively short period of time of about 24 hours.

Comparative Example 1

The crystals containing 12.6% by weight of isopropyl alcohol obtained in Example 2 were dried for the same period of time as in Example 2, i.e. 18 hours, under reduced pressure of 1 to 3 mm Hg and at 70° C. However, the content of isopropyl alcohol was 9.6% by weight.

From the above facts, it can be seen that in the process of Comparative Example 1, the content of isopropyl alcohol cannot be sufficiently reduced owing to the fact that the temperature during drying under reduced pressure is lower than the temperature in Example 2 (80° C.).

Comparative Example 2

The paroxetine hydrochloride anhydrate containing 53.5% by weight of isopropyl alcohol obtained in Example 1 was dried for 13 hours at 90° C. under reduced pressure of 54 to 85 mm Hg. As a result, a part of the crystals was melted, and its crystal form was deformed.

From the above facts, it can be seen that in Comparative Example 2, the crystals of paroxetine hydrochloride anhydrate were deformed because drying was carried out at a high temperature of not less than 80° C. before the content of isopropyl alcohol attains to not more than 15% by weight.

Comparative Example 3

In 317 g of isopropyl alcohol having a water content of 1% was dissolved 57.26 g (0.1565 mol) of paroxetine hydrochloric acid anhydride with heating, and the solution was cooled to allow crystallization. The resulting crystals were collected by filtration, washed with 99% isopropyl alcohol, and dried to give 49.7 g of crystals of paroxetine hydrochloride (yield: 84.7%).

The resulting crystals were subjected to IR analysis to determine its water amount. As a result, the crystals were found to be paroxetine hydrochloride hemihydrate.

Therefore, it can be seen that according to the process of Comparative Example 3, the crystal form of the paroxetine hydrochloride anhydrate cannot be obtained.

According to the process for drying paroxetine hydrochloride anhydrate of the present invention, there can be exhibited an excellent effect that the amount of remaining isopropyl alcohol contained in the paroxetine hydrochloride anhydrate can be efficiently reduced in a short period of time without using a large-scaled apparatus.

INDUSTRIAL APPLICABILITY

The paroxetine hydrochloride anhydrate obtained by the process of the present invention can be suitably used as intermediates for antidepressants.

What is claimed is:

1. A process for drying paroxetine hydrochloride anhydrate comprising:
    (A) reacting a paroxetine compound with hydrogen chloride in the presence of isopropyl alcohol and crystallizing the resulting product, to obtain paroxetine hydrochloride anhydrate;
    (B) drying the resulting paroxetine hydrochloride anhydrate at a temperature of 20° to 50° C. and under atmosphere having a relative humidity at 20° C. of not more than 10% until the content of isopropyl alcohol attains to 8 to 15% by weight; and
    (C) further drying the paroxetine hydrochloride anhydrate at a temperature of 80° to 110° C. in an atmosphere reduced to not more than 20 mm Hg until the content of isopropyl alcohol attains to not more than 5% by weight.

2. The process according to claim 1, wherein the paroxetine compound is paroxetine or N-tert-butoxycarbonylparoxetine.

3. The process according to claim 1, wherein the water content in isopropyl alcohol is not more than 0.1% by weight in the step (A).

4. The process according to claim 1, wherein the paroxetine hydrochloride anhydrate is dried until the content of isopropyl alcohol attains to 2.0 to 5.0% by weight.

5. A process for drying paroxetine hydrochloride anhydrate comprising:

(A) drying paroxetine hydrochloride anhydrate containing isopropyl alcohol at a temperature of 20° to 50° C. and under atmosphere having a relative humidity at 20° C. of not more than 10% until the content of isopropyl alcohol attains to 8 to 15% by weight; and (B) further drying the paroxetine hydrochloride anhydrate at a temperature of 80° to 110° C. in an atmosphere reduced to not more than 20 mm Hg until the content of isopropyl alcohol attains to not more than 5% by weight.

* * * * *